United States Patent [19]

Ferber et al.

[11] Patent Number: 5,149,719
[45] Date of Patent: Sep. 22, 1992

[54] COMPOSITION FOR TRANSDERMAL PENETRATION OF MEDICAMENTS

[75] Inventors: Richard H. Ferber; Scott A. Burton, both of St. Paul, Minn.

[73] Assignee: Minnesota Mining and Manufacturing Company, St. Paul, Minn.

[21] Appl. No.: 515,198

[22] Filed: Apr. 27, 1990

[51] Int. Cl.$^5$ .............................................. A61K 47/00
[52] U.S. Cl. ................................. 514/772; 514/947
[58] Field of Search ................................ 514/947, 772

[56] References Cited

U.S. PATENT DOCUMENTS

| | | | |
|---|---|---|---|
| 4,006,218 | 2/1977 | Sipos | 424/54 |
| 4,321,257 | 3/1982 | Sipos | 424/80 |
| 4,593,048 | 6/1986 | Sato et al. | 514/778 |
| 4,615,699 | 10/1986 | Gale et al. | 604/897 |
| 4,645,502 | 2/1987 | Gale et al. | 604/896 |
| 4,752,612 | 6/1988 | Saito et al. | 514/420 |

FOREIGN PATENT DOCUMENTS

| | | |
|---|---|---|
| 043738 | 1/1982 | European Pat. Off. |
| 127468 | 5/1984 | European Pat. Off. |
| 171742 | 2/1986 | European Pat. Off. |
| 255485 | 2/1988 | European Pat. Off. |
| 267617 | 5/1988 | European Pat. Off. |
| 271983 | 6/1988 | European Pat. Off. |
| 62-230710 | 10/1987 | Japan |
| 63-35521 | 2/1988 | Japan |
| 2075837 | 11/1981 | United Kingdom |
| 2098865 | 12/1982 | United Kingdom |
| 2128087B | 9/1986 | United Kingdom |
| 2194147 | 3/1988 | United Kingdom |

OTHER PUBLICATIONS

Sugibayashi et al., *Chem. Pharm. Bull.*, 36(4): 1519–1528 (1988).

Primary Examiner—Leonard Schenkman
Attorney, Agent, or Firm—Gary L. Griswold; Walter N. Kirn; Paul W. Busse

[57] ABSTRACT

A composition, and method of preparing such a composition, useful for the enhancement of the transdermal delivery of a medicament. The composition includes a medicament suspended in an aqueous solution of lower alcohol, to which solution is added an amount of higher alcohol sufficient to substantially saturate the composition.

6 Claims, No Drawings

COMPOSITION FOR TRANSDERMAL PENETRATION OF MEDICAMENTS

TECHNICAL FIELD

The present invention relates to the use of chemical penetration enhancers to enhance the transdermal delivery of medicaments and other molecules into and/or through the skin. In another aspect the invention relates to formulations containing such enhancers in combination with the medicament to be delivered. In particular the invention relates to formulations that include the use of alcohols as enhancers.

BACKGROUND OF THE INVENTION

A variety of systems have been described to enhance the transdermal flux of various bioactive molecules across the skin barrier. Compositions have been described containing chemical penetration enhancers from such diverse groups as alkanes, alkenes, amides, amines, amine oxides, carboxylic acids, esters, ethers, halocarbons, ketones, and sulfoxides.

Chemical penetration compositions have also been described that, for one purpose or another, involve the use of either lower or higher alcohols, or occasionally both lower and higher alcohols. See, e.g., U.S. Pat. Nos. 4,593,048 (Sato et al.), 4,615,699 (Gale et al.), 4,645,502 (Gale et al.), and 4,752,612 (Saito et al.), GB Patent Application Nos. 2,075,837 (Noda et al.), GB Patent Application No. 2,098,865 (Franz) and 2,194,147 (Sato et al.), Japanese application Kokai No. JP63-35521 (Ohtsuka et al.), and European Patent Application Publication Nos. 043,738 (Wickett et al.), 127,468 (Yamada et al.), 255,485 (Mahjour et al.), 267,617 (Patel et al.), and 271,983 (Francoeur et al.), as well as Sugibayashi et al., Chem. Pharm. Bull., 36(4):1519–1528 (1988).

Exemplary compositions involving the use of both lower and higher alcohols in an aqueous system include U.S. Pat. No. 4,006,218 (Sipos). The '218 patent describes topical compositions that include, inter alia, a potentiator that is used at a range described as between at least 0.05% (by weight) and about 15 to 18%, and preferably from about 1% to about 12% by weight of the composition. Suitable potentiators include, for instance, the alcohols described in Group I therein.

Example 6 of the '218 patent describes topical compositions containing, inter alia, ethanol at a concentration of 50% by weight, as well as various potentiators, each at a concentration of 10%. As can be seen by the results in TABLE III of the '218 patent, the potentiators coming within the definition of Group I of that patent (i.e., pentanol, hexanol, heptanol, and 2-heptanol) fared poorly compared to other potentiators. It can be determined in retrospect that for each Group I potentiator used, its concentration (i.e., 10%) was below the concentration that would saturate the respective composition. This is either because the saturating concentration was higher than the concentration actually used for a particular potentiator, or because the particular potentiator was infinitely miscible in the particular system, and therefore would have no saturating concentration.

U.K. Patent No. GB 2 128 087B (Asche et al.) describes topically administrable anti-inflammatory pharmaceutical compositions containing, together with other required ingredients, from 10 to 50% by weight of a water-soluble, volatile lower alkanol having from 2 up to and including 4 carbon atoms, and a lipid component that can include saturated or unsaturated fatty alcohols having, for example, 1 or 2 hydroxy functions and a carbon atom number of approximately from 6 to 34.

Japanese Kokai No. J62-230710 (Hori, et al.) describes the use of a number of penetration enhancement agents for use in a hair tonic with the hair growth compound minoxidil. The agents described include $C_7$ to $C_{15}$ alcohols, used at between 0.01 and 20% by weight of minoxidil. The exemplified formulation also contains ethanol at a concentration of 44.5% by weight.

No reference appears to use both an aqueous solution of lower alcohol together with higher alcohol used at a substantially saturated level, nor therefore do the references teach or suggest the advantages to be gained by the use of such a composition.

SUMMARY OF THE INVENTION

The present invention provides a composition useful for the enhancement of the transdermal delivery of a medicament, comprising an effective amount of the medicament suspended in (a) a formulation comprising an aqueous solution of lower alcohol, where the concentration of the lower alcohol is between about 0% and about 40% by volume of the solution, and (b) higher alcohol present in an amount that is sufficient to substantially saturate the composition.

In a preferred embodiment, higher alcohol is provided in an amount that is slightly in excess of saturation, e.g., such that a visible phase separation occurs between the saturated composition and the excess amount (e.g., reservoir) of higher alcohol. In this manner, as higher alcohol is absorbed from the composition into the skin in the course of transdermal delivery, the reservoir of higher alcohol is able to continually replenish the composition, thereby maintaining the composition in a substantially saturated form.

Compositions of the present invention are useful with a wide variety of medicaments, often exhibiting transdermal flux that is enhanced as much as 100 fold or more over the flux achievable without the use of the compositions. Moreover, preferred compositions are stable, non-irritating, and effective for prolonged transdermal delivery of medicaments.

In another aspect, the present invention provides a method of preparing a composition useful for the enhancement of the transdermal delivery of a medicament. The method involves the steps of (a) suspending an effective amount of the medicament in a formulation comprising an aqueous solution of lower alcohol, where the concentration of the lower alcohol is between about 0% and about 40% by volume of the solution, and (b) adding higher alcohol in an amount that is sufficient to substantially saturate the composition.

DETAILED DESCRIPTION

Unless otherwise noted, as used herein the word "solution" refers to the combination of lower alcohol and water; the word "formulation" refers to a solution containing medicament; and the word "composition" refers to a formulation substantially saturated with higher alcohol, optionally including other ingredients such as gel-, cream-, or ointment-forming ingredients.

The solution of the present invention includes one or more lower alcohols present at a total concentration of between about 0% to about 40% by volume, based on the volume of the solution. Suitable lower alcohols for use in the present invention exhibit an optimal combination of such properties as solubility in water, biocompatibility, pharmacologic acceptability, volatility, and cost.

Examples of suitable lower alcohols include ethanol, 1-propanol, 2-propanol, 1-butanol, 2-butanol and combinations thereof. Preferred lower alcohols for use in the present invention include ethanol, 2-propanol and combinations thereof.

Preferably, one or more lower alcohols are used at a final total concentration (based on the volume of the solution) of about 0% to about 40%, preferably about 10% to about 35%, and most preferably about 20% to about 30%. Concentrations above about 40% tend to be irritating to the skin, whereas concentrations nearing zero, e.g., those lower than about 10%, tend to result in lower transdermal fluxes than are desired.

A composition of the present invention includes a formulation (i.e., a medicament-containing aqueous solution of lower alcohol) as described herein, together with one or more higher alcohols present in an amount that is sufficient to substantially saturate the composition. Suitable higher alcohols for use in a composition of the present invention exhibit an optimal combination of such properties as carbon chain length, solubility, biocompatibility, and the like. In particular, the higher alcohol should not be infinitely miscible with the composition with which it is to be used, i.e., it must be capable of saturating the composition.

Preferred higher alcohols include, but are not limited to: (a) aliphatic straight or branched chain primary, secondary, and tertiary monohydric alcohols wherein the straight chain alcohols have from about 5 to about 14 carbon atoms; and the branched chain alcohols have up to about 14 carbon atoms, their longest straight chain of carbon to carbon bonds having from about 4 to about 10 carbon atoms; and (b) cyclic monohydric alcohols having from about 5 to about 17 carbon atoms and optionally including a ring of about 4 to about 6 carbon atoms.

Examples of preferred higher alcohols include, but are not limited to, 1-hexanol, 1-octanol, 1-nonanol, 1-decanol, 1-undecanol, 1-dodecanol, 1-tridecanol, 1-tetradecanol, 4-methyl-1-pentanol, 5-methyl-1-heptanol, 3,3-dimethyl-1-octanol, 3-cyclopentyl-1-propanol, cis-3-hexen-1-ol, trans-3-hexen-1-ol, 9-decen-1-ol and 2-octanol.

Higher alcohol is used in the present invention at a total concentration such that higher alcohol substantially saturates the composition. Preferably higher alcohol is present at a total concentration slightly in excess of that needed to substantially saturate the composition. In this manner the slight excess preferably maintains the saturation of the composition in the course of transdermal delivery. For example, in the event higher alcohol is removed from the composition into the skin in the course of delivery, saturation of the remaining composition can be maintained by virtue of the slight excess present.

The word "substantially" in this respect means that the addition of an incremental amount, e.g., an additional 10% of the amount already added, of higher alcohol causes a visible phase separation of a portion of the higher alcohol. It will become apparent to those skilled in the art, as illustrated in the EXAMPLES below, that the saturating concentration of a particular higher alcohol will vary depending on the amount and types of other components in the composition, particularly the lower alcohol and medicament.

The ability of a higher alcohol to form a substantially saturated composition using a particular formulation, and in turn the amount of higher alcohol necessary to form a slight excess of higher alcohol, can be easily determined by those of ordinary skill in the art. For instance, by incrementally adding small amounts of higher alcohol to a formulation until cloudiness appears upon shaking, and a visible separation of phases occurs as the cloudy composition is allowed to sit.

The formulation of the present invention comprises an effective amount of medicament suspended in an aqueous solution of lower alcohol, as described herein. The word "suspended", as used herein, refers to any physical form of medicament in a solution that enables the resulting formulation to be saturated with higher alcohol and used for transdermal delivery of the medicament. For example, the medicament can be present in the form of a solution, emulsion, or colloid.

Medicaments suitable for use in formulations of the present invention exhibit an optimal combination of such properties as water solubility, polarity, structure, and molecular weight, for instance, molecular weights between about 100 daltons and about 5000 daltons, and preferably between about 200 daltons and about 1200 daltons. Examples of suitable medicaments include those described in U.S. Pat. No. 4,752,612, the disclosure of which is incorporated herein by reference.

Examples of preferred medicaments include calcium channel blocking agents such as diltiazem HCl and verapamil HCl; beta-blocking agents such as timolol maleate, sympathomimetic drugs, e.g., bronchodilators such as pirbuterol HCl and albuterol $SO_4$; analgesics such as morphine; antihistamines such as chlorpheniramine HCl, phenylpropylamine HCl, and diphenylpyraline HCl; and antipsychotics such as haloperidol.

An effective amount of medicament is used, i.e., an amount effective to provide the desired flux when delivered transdermally from a composition of the present invention. The amount of medicament can be determined by those skilled in the art for a particular composition, in consideration of the transdermal delivery approach to be used and desired dose to be delivered.

Compositions of the present invention can be prepared in any suitable manner, e.g., by combining the ingredients at room temperature according to techniques within the skill of those in the art. Preferably the aqueous solution of lower alcohol is prepared first, followed by the addition of medicament in order to prepare a formulation. A composition can then be prepared by adding a saturating amount of higher alcohol to the formulation.

Compositions can be stored according to common techniques useful with other compositions of a like nature, e.g., refrigerated and in a closed vessel. Compositions of the present invention can be used in any suitable manner. Generally the formulations will be warmed, e.g., to about 32° C. and applied to the skin, e.g., in a vehicle, from a matrix, or in combination with a device.

Compositions can be applied to the skin in any suitable form, e.g., in the form of a liquid; a viscid aqueous solution such as a mucilage or jelly; an emulsion, including an oil-in-water emulsion and a water-in-oil emulsion; or a suspension such as a gel, lotion, or mixture. See, e.g., J.G. Nairn, in "Remington's Pharmaceutical Sciences" (A.F. Gennaro, ed.) 17th edition, Mack Publishing Co., Easton, PA, pp. 1492-1517, the disclosure of which is incorporated herein by reference.

Alternatively, compositions of the present invention can be used in combination with transdermal delivery systems, such as reservoir systems with rate-controlling membranes, including microencapsulation, macroencapsulation, and membrane systems; reservoir systems without rate-controlling membranes (such as hollow fibers, microporous membranes and porous polymeric substrates and foams); monolithic systems including those where the composition is physically dispersed in a nonporous polymeric or elastomeric matrix; and laminated structures including those where the reservoir layer is chemically similar to outer control layers and those where the reservoir layer is chemically dissimilar to outer control layers. (See, e.g., A.F. Kydonieus and B. Berner, eds.) CRC Press, Inc., Boca Raton, FL, 1987, pp 3–16, the disclosure of which is incorporated herein by reference.

Compositions of the present invention can include optional ingredients, e.g., those commonly used with transdermal compositions, such as antioxidants and preservatives, coloring and diluting agents, emulsifying and suspending agents, ointment bases, thickeners, and fragrances. See, e.g., E.A. Swinyard and W. Lowenthal in "Remington's Pharmaceutical Sciences" (A.F. Gennaro, ed.) 7th edition, Mack Publishing Co., Easton, PA 1985, pp. 278–1320, the disclosure of which is incorporated herein by reference.

The following EXAMPLES are provided to illustrate, but not limit, the scope of the invention. Unless otherwise indicated, all percentages are by volume (i.e., "v/v"), and ethanol was used as reagent grade 95% (i.e., not absolute) ethanol.

EXAMPLES

TEST METHOD A

General Procedures for Transdermal Delivery Studies

Transdermal delivery was evaluated by in vitro permeation studies performed either over the course of 8 hours or 24 hours, as specified in the EXAMPLES below, according to the following method.

Full thickness skin from hairless guinea pig was placed between two chambers of a Valia-Chien diffusion cell (Vangard International, Inc., Neptune, NJ). The receiver chamber of the diffusion cell contained phosphate-buffered saline ("PBS") (0.04M phosphate buffer, 1.032M NaCl, 0.032M $NaN_3$, pH 7.4). In each case the donor cell contained the composition.

Both chambers were stoppered and maintained at 32° C., and were stirred continuously at approximately 600 rpm with a magnetic stirrer. A volume of 3.75 ml of test material and receiver material was used in each chamber. A sample of 10μl was taken from the donor chamber, and a sample of 1 ml was taken from the receiver chamber every two hours, i.e., at 18, 20, 22, and 24 hours. After taking each 1 ml sample from the receiver chamber, this volume was made up by adding a 1 ml aliquot of the same fresh buffer that the chamber originally contained.

The test samples were analyzed either by high pressure liquid chromatography ("HPLC") as described below, or by radioassay according to the method described in the operations manual for the Tri-Carb 460CD Liquid Scintillation System (Packard Instrument Co., Downers Grove, IL). Unless otherwise indicated, n =4 for each sample.

Data reduction was performed by computer. The output from both the HPLC apparatus and the radiation counter were converted directly to permeability coefficients, fluxes, and lag times. These values are provided in the EXAMPLES below.

TEST METHOD B

Assay of Diltiazem HCl by HPLC

An HPLC apparatus (Spectra-Physics, Inc., San Jose, CA) consisting of an "SP4290" integrator, an "SP8700XR" pump system, an "SP8780" autosampler and a Kratos Spectraflow ™ variable wavelength absorption detector was used to determine the level of diltiazem in samples taken above. The HPLC column was 15 cm ×4.6 cm internal diameter, loaded with Supelcosil ™ "LC-8-DB" of 5 μm particle size (Supelco, Inc., Supelco Park, Bellefonte, PA, 16823). No guard column was used. The flow rate was 1.0 ml/minute; the detector was set at 254 nm at 0.05 AUFS; and the run time was 8 minutes.

Mobile Phase Preparation. For preparation of the mobile HPLC phase, potassium dihydrogen phosphate ($KH_2PO_4$), 2.72 gms, was dissolved in 1 liter of HPLC-grade water. Triethylamine (100 μl ) was added with mixing. The pH was adjusted to 3.4 with phosphoric acid and used as the HPLC buffer. To 600 ml of this buffer was added 400 ml of HPLC grade acetonitrile. The acetonitrile-containing buffer was then filtered through a 0.45 μm nylon filter, and degassed with helium.

Assay of Samples. Samples (10 μl ) from the donor chamber were added to 1.99 ml of water, which in turn was further diluted with 2 ml of the mobile phase acetonitrile-containing buffer prepared above. Samples (1 ml) from the receiver chamber were diluted with a further 1 ml of mobile phase acetonitrile-containing buffer. Each diluted sample was filtered through a 0.45 μl nylon filter into a HPLC sample vial.

Standards consisted of 1, 10, 100, and 1000 μg of diltiazem hydrochloride dissolved in the respective concentrations of aqueous phase/mobile phase used for the unknown samples.

TEST METHOD C

Assay of Albuterol Sulfate by HPLC

The apparatus was the same as in TEST METHOD B above, with the exception that a 2 cm LC-8-DB guard column was used ahead of the main column. The flow rate was 1.0 ml/minute. The detector was set at 237 nm at 0.05 absorption units full scale ("AUFS"). The run time was 10 minutes.

Mobile Phase Preparation. 1 gm of heptane sulfonic acid, sodium salt, was dissolved in 790 ml of HPLC grade water. To this solution was added 200 ml of HPLC grade acetonitrile, and 10 ml of glacial acetic acid. After mixing, the solution was filtered through a 0.45 μm nylon filter, and then degassed.

Assay of Samples. The procedure was the same as that described in TEST METHOD B, substituting albuterol sulfate for diltiazem hydrochloride throughout.

TEST METHOD D

Assay of Pirbuterol by HPLC

The apparatus was the same as in TEST METHOD B, with the exception that a 2 cm LC-8-DB guard column was used. The flow rate was 1.0 ml/minute. The detector was set at 237 nm at 0.05 AUFS. The run time was 7 minutes.

Mobile phase preparation. 1 gm of 1-heptane sulfonic acid, sodium salt, was dissolved in 690 ml of HPLC-grade water. To this solution was added 300 ml of HPLC-grade acetonitrile, and 10 ml of glacial acetic acid. After mixing, the solution was filtered through a 0.45 μm nylon filter, and then degassed.

Assay of samples. The procedure was the same as that of the preceding TEST METHODS, substituting pirbuterol hydrochloride throughout.

TEST METHOD E

Assay of Timolol Maleate

The apparatus was the same as in TEST METHOD B, with the exception that the HPLC column was 220 mm ×4.6 mm from Brownlee Lab #ODS-224 of 5 μm particle size (purchased from Chrom Tech, Apple Valley, MN). The flow rate was 1.5 ml/minute. The detector was set at 254 nm at 0.05 AUFS. The run time was 10 minutes.

Mobile phase preparation. 8.71 g of potassium phosphate were dissolved in 1 liter of HPLC-grade water. The pH was adjusted to 3.0 with phosphoric acid. To 840 mls of this solution were added 100 μl of triethylamine and 150 mls of HPLC-grade acetonitrile. This solution was filtered through a 0.45 μm nylon filter, and then degassed.

Assay of samples. The test procedure was the same as that of the previous TEST METHODS, substituting timolol maleate throughout.

TEST METHOD F

Assay for Diphenylpyraline HCl

The apparatus was the same as in TEST METHOD B, with the exception that a 2 cm LC-8-DB guard column was used. The flow rate was 1.5 ml/minute. The detector was set at 214 nm at 0.05 AUFS. The run time was 10 minutes.

Mobile phase preparation. 6.805 gms of potassium dihydrogen phosphate were dissolved in 1 liter of HPLC-grade water. To 530 mls of this solution were added 200 μl of triethylamine and 450 mls of HPLC-grade acetonitrile. This solution was filtered through a 0.45 μm nylon filter and degassed.

Assay of samples. The procedure was the same as that of the previous TEST METHODS, substituting diphenylpyraline HCl throughout.

TEST METHOD G

Assay of Phenylpropanolamine HCl

The apparatus was the same as in TEST METHOD B, with the exception that the column was the same as in TEST METHOD D. The flow rate was 1.5 ml/minute. The detector was set at 254 nm at 0.2 AUFS. The run time was 10 minutes.

Mobile phase preparation. To 920 mls of HPLC-grade water were added 60 mls of HPLC-grade methanol, 15 mls of glacial acetic acid and 5 mls of triethylamine. This solution was filtered through a 0.45 μm nylon filter and then degassed.

Assay of samples. The procedure was the same as that of previous TEST METHODS, substituting phenylpropanolamine HCl throughout.

TEST METHOD H

Assay of Samples by Radiotracer Technique

Where indicated below tritium-radiolabeled samples of the material to be assayed were used according to the following procedure.

A 10 μl sample of the donor chamber was used. It was added to 10 ml of scintillation cocktail ("Ready Solv-HP", Beckman Instrument Co., containing 1 ml of standard buffer, prepared as described in TEST METHOD A). A 1 ml sample of the receiver chamber was added to 10 ml of the scintillation cocktail, without added buffer. Samples were counted in a beta counter (model "Tri-carb #460 CD", Packard) for assay of the radioactive material present.

EXAMPLE 1

Transdermal Delivery of H:-Mannitol

A 30% v/v solution of ethanol (95%, reagent grade) in water was used. A stock formulation of tritiated mannitol (New England Nuclear Research Products, Boston, MA) was prepared by dissolving a radiotracer amount (5 microliters, specific activity 1 mCi/ml) of $H^3$-mannitol in 25 ml of the ethanol solution. Mannitol (MW 182.2) is frequently used as a test molecule for transdermal delivery, in part since it is stable, highly polar, water soluble, not metabolized by the skin, and relatively inexpensive. An excess of pentanol (previously determined for this formulation to be 100 μl/ml) was then added, resulting in a composition of mannitol in a solution saturated with pentanol, and having a slight excess of pentanol. This composition was kept at 32° C. until use.

For testing, the composition was agitated to resuspend the excess pentanol (forming a cloudy product), and 3.5 ml samples were removed and transferred to the donor chamber of a Valia-Chien diffusion cell and tested for transdermal delivery of the drug according to TEST METHOD A and assayed as in Test Method H.

EXAMPLES 2–10

Effect of Higher Alcohols

These EXAMPLES disclose the preparation and testing of transdermal compositions of tritiated mannitol in solutions of 30% v/v aqueous ethanol together with respectively, excess saturated amounts of hexanol, octanol, nonanol, decanol, dodecanol, tridecanol, tetradecanol, hexadecanol, and octadecanol.

In these EXAMPLES, the procedure of EXAMPLE 1 was followed, with the exception that the formulation of $H^3$-mannitol in aqueous ethanol was then saturated with, respectively, one of the higher alcohols identified above.

In practice, the alcohols were added until a small permanent excess was visible. The amounts necessary to reach this point were approximately: hexanol 30 μl/ml, octanol 20 μl/ml, nonanol 10 μl/ml, decanol 10 μl/ml, dodecanol 10 μl/ml, tridecanol 4 mg/ml, tetradecanol 4 mg/ml, hexadecanol 0.1 mg/ml, and octadecanol 0.1 mg/ml.

Again, the data were reduced by computer as described above, and are shown in TABLE 1 below. The data are for steady-state measurements made at 24 hours after starting transdermal delivery. The permeability coefficient is in units of cm/hr, and "SEM" refers to Standard Error of the Mean.

TABLE 1

| EXAMPLE No. | Higher Alcohol | Permeability Coefficient (cm/hr) ± SEM |
|---|---|---|
| Control | none | $1.14 \times 10^{-4} \pm 0.405 \times 10^{-4}$ |
| 1 | pentanol | $4.04 \times 10^{-2} \pm 0.55 \times 10^{-2}$ |
| 2 | hexanol | $1.79 \times 10^{-2} \pm 0.42 \times 10^{-2}$ |
| 3 | octanol | $2.19 \times 10^{-2} \pm 0.62 \times 10^{-2}$ |
| 4 | nonanol | $1.77 \times 10^{-2} \pm 0.27 \times 10^{-2}$ |
| 5 | decanol | $1.16 \times 10^{-2} \pm 0.33 \times 10^{-2}$ |
| 6 | dodecanol | $4.57 \times 10^{-3} \pm 1.23 \times 10^{-3}$ |
| 7 | tridecanol | $1.49 \times 10^{-3} \pm 0.30 \times 10^{-3}$ |
| 8 | tetradecanol | $5.67 \times 10^{-4} \pm 3.67 \times 10^{-4}$ |
| 9 | hexadecanol | $9.83 \times 10^{-5} \pm 5.96 \times 10^{-5}$ |
| 10 | octadecanol | $1.02 \times 10^{-4} \pm 0.51 \times 10^{-4}$ |

As can be seen in TABLE 1, when used at a saturating level each of the higher alcohols, up to and including tetradecanol, produced an increase in the permeability coefficient of tritiated mannitol of from about 13 fold to about 386 fold.

EXAMPLE 11

Transdermal Delivery of Diltiazem HCl

Diltiazem hydrochloride (902 mg) was dissolved in 10 mls (final conc. 0.2M) of a 25% v/v aqueous ethanol solution. After all the drug had completely dissolved, a slight excess of octanol (previously determined to be 100 μl ) was added in order to obtain a composition saturated with octanol together with a slight excess. The composition was maintained in a water bath at 32° C. until use. A control was prepared in the same manner, although omitting octanol.

Aliquots of the composition were tested for transdermal delivery, and diltiazem determined, according to TEST METHODS A and B. The results are shown in TABLE 2.

EXAMPLE 12

Transdermal Delivery of Diltiazem HCl from a Gel

A: This EXAMPLE describes making and testing the composition of EXAMPLE 11 prepared in the form of a hydrogel of cross-linked polyvinylpyrrolidone.

A composition containing diltiazem hydrochloride was prepared as a gel ("hydrogel I" below) according to the method described in co-pending U.S. Pat. application Ser. No. 125,377, filed Nov. 25, 1987, the disclosure of which is incorporated herein by reference. One gram of polyvinyl pyrrolidone powder were added to the composition (approx. 10 ml) at a temperature of 32° C, followed by rapid mixing for 30 seconds. As a control, identical gels were prepared although omitting the use of higher alcohol from the composition. The resulting hydrogel I and its control were kept in capped containers in a water bath at 32° C. for 16 hours before use.

Transdermal delivery using a hydrogel was evaluated using a special donor chamber for the earlier described Valia-Chien diffusion cell. A 5 ml plastic disposable syringe was modified to fit the cell and to deliver hydrogel to the skin surface. 0.5 ml of the hydrogel was placed in the syringe, and transdermal delivery was evaluated according to TEST METHOD B. Sampling of the receiver chamber was performed as described above in TEST METHOD A.

The data were reduced by computer as before, and are shown in TABLE 2 below.

As can be seen from TABLE 2, the enhancement of the flux of diltiazem HCl from a composition of the present invention in the form of a hydrogel, although lower than the delivery achieved using a non-gelled composition, was still greater than the delivery achieved using control (i.e., a gel not containing higher alcohol). It appears that the increase in viscosity of the hydrogel compared to the non-gelled composition may impede the diffusion of drug within and from the hydrogel.

B: A composition and corresponding control lacking higher alcohol was prepared and evaluated as described in EXAMPLE 11 in the form of a hydrogel of cross-linked polyvinylpyrrolidone, with the exception that the formulation was prepared using 1804 mg of diltiazem HCl dissolved in 10 ml 40% v/v aqueous ethanol (final conc. 0.4M), after which 400 μl of octanol was added to saturate the composition and form a slight excess.

The hydrogel (hydrogel "II") and its control were used in the same manner of those of Part A above. Results are provided in TABLE 2 below.

TABLE 2

Transdermal Delivery of Diltiazem HCl

| EXAMPLE No. | Permeability Coefficient (cm/hr) ± SEM | Flux (mg/cm²/hr) |
|---|---|---|
| 11 control | $3.70 \times 10^{-5} \pm 1.04 \times 10^{-5}$ | $3.34 \times 10^{-3}$ |
| 11 composition | $2.38 \times 10^{-2} \pm 0.53 \times 10^{-2}$ | $2.14 \times 10^{0}$ |
| 12A control | $1.80 \times 10^{-5} \pm 0.10 \times 10^{-5}$ | $1.62 \times 10^{-3}$ |
| 12 hydrogel I | $7.17 \times 10^{-3} \pm 3.92 \times 10^{-3}$ | $6.49 \times 10^{-1}$ |
| 12B control | $3.00 \times 10^{-6} \pm 2.00 \times 10^{-6}$ | $5.41 \times 10^{-4}$ |
| 12 hydrogel II | $2.61 \times 10^{-3} \pm 0.23 \times 10^{-3}$ | $4.71 \times 10^{-1}$ |

The term "permeability coefficient", as used herein, refers to permeability in cm/hr, and the word "flux", as used herein, refers to flux in mg/cm²/hr.

As can be seen from TABLE 2, the enhancement of the flux of diltiazem HCl from an aqueous composition or from a hydrogel, over the corresponding control of each, is significant. The increase in flux ranges from about 640 fold for the aqueous composition to about 400 and 870 fold, respectively, from the hydrogels.

EXAMPLE 13

Effect of Lower Alcohol Concentration

In this study a saturating amount of dodecanol was used. The ethanol concentration of each composition was varied as shown below. The diltiazem hydrochloride concentration was 541 mg/ml. Other parameters and processes were as previously described.

TABLE 3

Effect of Varying Lower Alcohol Concentration on Transdermal Delivery of Diltiazem Hydrochloride

| [Ethanol] (v/v) | Permeability Coefficient (cm/hr) ± SEM | Flux (mg/cm²/hr) |
|---|---|---|
| 50% | $1.06 \times 10^{-3} \pm 0.11 \times 10^{-3}$ | 0.55 |
| 40% | $1.15 \times 10^{-3} \pm 0.32 \times 10^{-3}$ | 0.60 |
| 30% | $3.33 \times 10^{-4} \pm 0.06 \times 10^{-4}$ | 0.17 |
| 20% | $1.21 \times 10^{-4} \pm 0.30 \times 10^{-4}$ | 0.06 |
| none | $2.75 \times 10^{-5} \pm 1.49 \times 10^{-5}$ | 0.01 |

The results in TABLE 3 show that over 8 hours, decreasing the lower alcohol concentration appeared to decrease the permeability of the skin to the drug. As described further below, however, when the lower alcohol concentration is low, e.g., less than about 40% v/v, 8 hours is generally insufficient time to reach an equilibrium for the passage of drug through the skin. In the following EXAMPLES, experiments are described that extend out to 24 hours.

EXAMPLE 14

Transdermal Delivery of Pirbuterol Hydrochloride

A 30% solution of ethanol in water was used. A stock formulation of pirbuterol hydrochloride was made up by dissolving 480 mg of the drug in 10 ml of this aqueous ethanol solution. When the drug was fully dissolved, 0.04 ml of octanol was added in order to make a composition saturated and w.ith a slight excess of octanol. The composition was kept at 32° C. until use.

Aliquots of the composition were evaluated for transdermal delivery according to the method of TEST METHOD A. Pirbuterol was determined according to TEST METHOD D. Sample collection and data reduction were as described in EXAMPLE 1. The results are shown in TABLE 4 below.

EXAMPLES 15-17

These EXAMPLES disclose the preparation and evaluation of pirbuterol hydrochloride in compositions having varying concentrations of ethanol, all saturated and with a slight excess of octanol. The results are shown in TABLE 4. Delivery and pirbuterol determination were as described in EXAMPLE 14.

EXAMPLE 18

This EXAMPLE was performed as described in EXAMPLE 14, except that instead of ethanol a mixture of ethanol and isopropanol was used as the lower alcohol.

EXAMPLE 19

This EXAMPLE was performed as described in EXAMPLES 14-18, except that no lower alcohol was used. The drug was dissolved in pure water which was then saturated with octanol. In this sense, it acts as a control for the data given TABLE 4.

As used herein, the term "lag time" refers to the time required under each of the identified conditions for a steady state to be reached, i.e., such that the amount of drug entering the skin on the "donor" side of the testing apparatus was equal to the amount leaving the skin at the "receiver" side.

TABLE 4

Transdermal Delivery of Pirbuterol Hydrochloride

| EXAMPLE No. | Lower Alcohol Conc. | Permeability Coefficient (cm/hr) ± SEM | Flux (mg/hr/cm$^2$) | Lag Time (hrs) ± SEM |
|---|---|---|---|---|
| 19 (CONTROL) | 0% ethanol (v/v) | 7.11 × 10$^{-4}$ ±1.91 × 10$^{-4}$ | 0.032 | 12.04 ±0.43 |
| 15 | 10% ethanol | 1.79 × 10$^{-3}$ ±0.026 × 10$^{-3}$ | 0.086 | 12.2 ±0.16 |
| 16 | 20% ethanol | 1.17 × 10$^{-2}$ ±0.34 × 10$^{-2}$ | 0.56 | 9.19 ±0.64 |
| 17 | 25% ethanol | 2.13 × 10$^{-2}$ ±0.44 × 10$^{-2}$ | 1.02 | 6.02 ±0.98 |
| 14 | 30% ethanol | 1.97 × 10$^{-2}$ ±0.37 × 10$^{-2}$ | 0.95 | 2.63 ±2.4 |
| 18 | 12% ethanol 13% isopropanol | 1.3 × 10$^{-2}$ ±0.37 × 10$^{-2}$ | 0.62 | 10.14 ±1.58 |

As can be seen from TABLE 4, the various ethanol concentrations between 20% and 30%, inclusive, as well as the ethanol/isopropanol mixture each resulted in significant enhancement of the flux of pirbuterol HCl. At a concentration of 10% ethanol, the pirbuterol flux fell approximately 10 fold as compared to EXAMPLE 16, but was still about 3 fold higher than control. The greatest effect of lower alcohol concentration appeared to be on the lag time, in that the higher the ethanol concentration the shorter the lag time.

EXAMPLE 20

Transdermal Delivery of Pirbuterol Hydrochloride in a Gel

A hydrogel of cross-linked polyvinylpyrrolidone was prepared as described in EXAMPLE 12 using the following composition.

Pirbuterol hydrochloride (48 mg) was added to 1 ml of a 50% v/v solution of ethanol in water. After the salt was fully dissolved, approximately 60 μl of dodecanol, an excess, were added, and the composition was warmed to 32° C. The gelling agent (100 mg) was then added, with rapid stirring for 30 seconds after addition. A hydrogel formed and was kept in a closed container in a water-bath at 32° C. for 16 hours before use.

The hydrogel was evaluated by the method previously described by using 0.5 ml in a modified syringe as the donor chamber of a Valia-Chien apparatus. The results are shown in TABLE 5 below.

EXAMPLE 21

Effect of Hi9her Alcohol

This EXAMPLE, which acts as a control for EXAMPLE 20, describes making and testing a hydrogel without the use of dodecanol. The procedure was the same as that of EXAMPLE 20, except that dodecanol was omitted. In this study, the drug was dissolved in 50% v/v aqueous ethanol in each case.

The results are shown in TABLE 5 below.

It can be seen in TABLE 5 below that enhancement of pirbuterol HCl can also be achieved from a hydrogel prepared using a composition of the present invention.

TABLE 5

Transdermal Delivery of Pirbuterol Hydrochloride in the Presence and Absence of a Higher Alcohol

| EXAMPLE No. | Higher Alcohol | Permeability Coefficient (cm/hr) ± SEM | Flux (mg/hr/cm$^2$) |
|---|---|---|---|
| 20 | dodecanol | 3.34 × 10$^{-3}$ ±6.0 × 10$^{-4}$ | 0.160 |
| 21 | none | 4.60 × 10$^{-5}$ ±0.078 × 10$^{-5}$ | 0.0022 |

EXAMPLE 22

Transdermal Delivery of Albuterol Sulfate

Albuterol sulfate (478 mg) was dissolved in 10 ml of 25% (v/v) isopropanol/water solution to form a 0.2M formulation. Ascorbic acid (50 mg) was also added as an antioxidant. When all solids had dissolved, an excess of octanol (0.1 ml) was added. This composition was kept at 32° C. in a water bath until use. Sample collection, data reduction, and the assay for albuterol were as described in TEST METHODS A AND C. The results are shown in TABLE 6 below.

EXAMPLE 23

Effect of Higher Alcohol

This EXAMPLE, which acts as a control for EXAMPLE 22, describes the making and testing of a formulation without the use of octanol.

The procedure was the same as that of EXAMPLE 22, except that octanol was omitted. The results are shown in TABLE 6 below.

As can be seen in TABLE 6 a composition of the present invention is useful for increasing the flux of albuterol sulfate as well.

EXAMPLE 24

Transdermal Delivery of Albuterol Sulfate in a Hydrogel

A composition was prepared in the manner described in EXAMPLE 22. After preparation the composition was warmed to 32° C. and one gram of polyvinylpyrrolidone powder was added, and stirred for 30 seconds. The resulting hydrogel was then kept in a capped container for 16 hours at 32° C. before use. Testing and sampling of the hydrogel was then done by the method using a modified donor cell, described in EXAMPLE 12. The results are shown in TABLE 6 below.

As can be seen, delivery is enhanced in the sample with saturated amount of higher alcohol, as compared to the control of EXAMPLE 23.

EXAMPLE 25

Transdermal Delivery of Morphine

A composition was prepared in the manner of EXAMPLE 14, except that a radiotracer amount of tritiated morphine was used instead of pirbuterol hydrochloride.

The assay was performed as described in TEST METHODS A and H, the assay of samples by radiotracer technique. The results are shown in TABLE 6 below.

As can be seen, delivery is enhanced in the sample with saturated amount of higher alcohol, as compared to the control without higher alcohol.

EXAMPLE 26

Transdermal Delivery of Verapamil HCl

The test procedure used was that of EXAMPLE 25, except that a radiotracer amount of tritiated verapamil as the hydrochloride was used instead of morphine. The results are shown in TABLE 6 below.

As can be seen, delivery is enhanced in the composition with saturated amount of higher alcohol, as compared to the control without higher alcohol.

EXAMPLE 27

Transdermal Delivery of Timolol Maleate

A 25% v/v solution of isopropanol in water was used. A stock formulation of timolol maleate was made up by dissolving 1.73 gm of drug in 20 ml of this solution. When the drug was fully dissolved, 1.25 ml, an excess, of octanol was added to make a composition saturated with an excess of octanol. After the octanol was added, aqueous isopropanol was added to a final volume of 25 mls. This composition was kept at 32° C. until use.

Aliquots of the composition were evaluated for transdermal delivery according to TEST METHODS A and E. The results are shown in TABLE 6 below.

EXAMPLE 28

Transdermal Delivery of Diphenylpyraline Hydrochloride

A composition was prepared in the manner of EXAMPLE 27, substituting 1.27 gm of diphenylpyraline HCl for timolol maleate, and adding instead 2.1 ml of octanol.

Aliquots of the composition were evaluated transdermal delivery according to TEST METHODS A and F. The results are shown in TABLE 6 below.

EXAMPLE 29

Transdermal Delivery of Phenylpropanolamine Hydrochloride

A 20 ml composition was prepared in the manner of EXAMPLE 27, substituting 750.8 mg of phenylpropanolamine HCl for timolol maleate, and adding instead 1.62 ml of octanol.

Aliquots of the composition were evaluated for transdermal delivery according to TEST METHODS A and G. The results are shown in TABLE 6 below.

TABLE 6

Transdermal Delivery With and Without Higher Alcohol

| EXAMPLE No. | Medicament | Permeability Coefficient (cm/hr) ± SEM | |
|---|---|---|---|
| | | With Higher Alcohol | Without Higher Alcohol |
| 22, 23 | albuterol sulfate liquid | $1.79 \times 10^{-2}$ $\pm 1.23 \times 10^{-2}$ | $6.35 \times 10^{-5}$ $\pm 2.28 \times 10^{-5}$ |
| 24 | albuterol sulfate gel | $3.41 \times 10^{-3}$ $\pm 0.72 \times 10^{-3}$ | NP |
| 25 | morphine radiotracer | $6.80 \times 10^{-2}$ $\pm 1.43 \times 10^{-2}$ | $4.23 \times 10^{-5}$ $\pm 2.91 \times 10^{-5}$ |
| 26 | verapamil hydrochloride radiotracer | $4.71 \times 10^{-2}$ $\pm 0.58 \times 10^{-2}$ | $5.98 \times 10^{-4}$ $\pm 3.04 \times 10^{-4}$ |
| 27 | timolol maleate | $5.51 \times 10^{-2}$ $\pm 1.06 \times 10^{-2}$ | $1.89 \times 10^{-5}$ $\pm 0.09 \times 10^{-5}$ |
| 28 | diphenylpyraline hydrochloride | $2.45 \times 10^{-2}$ $\pm 0.35 \times 10^{-2}$ | $7.91 \times 10^{-5}$ $\pm 3.00 \times 10^{-5}$ |
| 29 | phenylpropanolamine hydrochloride | $7.78 \times 10^{-2}$ $\pm 0.62 \times 10^{-2}$ | $3.94 \times 10^{-3}$ $\pm 0.59 \times 10^{-3}$ |

NP = experiment not performed

EXAMPLES 30-37

Transdermal Delivery — Effect of Higher Alcohol

These EXAMPLES describe the evaluation of a number of compositions of the present invention. Mannitol was used throughout as the drug model, dissolved in 30% v/v ethanol/water solution as the lower alcohol. Formulations were prepared by adding tracer amounts of $H^3$-mannitol to the 30% v/v aqueous ethanol solution. An excess amount of higher alcohol was added. All compositions were kept in a water bath at 32° C. until use. Delivery was evaluated as described before (TEST METHODS A and H). The results are shown in TABLE 7 below.

TABLE 7

| Example No. | Higher Alcohol | Permeability Coefficient (cm/hr) ± SEM | Lag Time (hrs) ± SEM |
|---|---|---|---|
| Control | none | $6.67 \times 10^{-5}$ $\pm 1.15 \times 10^{-5}$ | 11.45 $\pm 0.83$ |
| 30 | cis-3-hexen-1-ol | $2.91 \times 10^{-2}$ $\pm 0.81 \times 10^{-2}$ | 15.70 $\pm 1.22$ |
| 31 | trans-3-hexen-1-ol | $2.79 \times 10^{-2}$ $\pm 1.05 \times 10^{-2}$ | 15.70 $\pm 1.35$ |
| 32 | 1-octanol | $2.74 \times 10^{-2}$ $\pm 0.36 \times 10^{-2}$ | 8.95 $\pm 0.75$ |
| 33 | 9-decen-1-ol | $6.16 \times 10^{-3}$ $\pm 0.59 \times 10^{-3}$ | 2.48 $\pm 0.04$ |
| 34 | 3-cyclopentyl-1-propanol | $1.45 \times 10^{-2}$ $\pm 0.41 \times 10^{-2}$ | 2.40 $\pm 0.15$ |
| 35 | 4-methyl-1-pentanol | $4.86 \times 10^{-2}$ $\pm 0.45 \times 10^{-2}$ | 3.18 $\pm 0.23$ |
| 36 | 5-methyl-1-heptanol | $2.80 \times 10^{-2}$ $\pm 0.95 \times 10^{-2}$ | 9.49 $\pm 1.76$ |
| 37 | 3,3-dimethyl-1-octanol | $4.87 \times 10^{-3}$ $\pm 0.99 \times 10^{-3}$ | 10.65 $\pm 2.04$ |

TABLE 7 shows that a variety of higher alcohols can be effectively used in the compositions of the present invention. Each composition of the invention exhibited an increase in the permeability coefficient of at least 70 to 730 fold over the corresponding control. The lag times for the compositions vary over a range from about two and one-half to eleven and one-half hours. Although the reason for such variability is not presently understood, the shorter lag times are generally preferred.

EXAMPLE 38

Transdermal Delivery at Saturated and Unsaturated Octanol Concentrations

Trace amounts of $H^3$-mannitol were added to 10 ml aliquots of a 33% (v/v) ethanol/water solution. The saturating amount of octanol for this solution was determined to be 45 µl per aliquot. Varying amounts of octanol were added to each aliquot as shown below. The aliquots were warmed and kept at 32° C. until use. Delivery was evaluated at 8 hours as described in TEST METHODS A AND H, and the results are shown in TABLE 8 below.

The octanol concentration was varied as follows: 0 µl = 0% saturation, 12 µl = 26.7% saturation; 25 µl = 55.6% saturation; 38 µl = 84.4% saturation; and 45 µl = 100% saturation, and 100 µl = 222.2% saturation.

TABLE 8

Effect of Varying Concentrations of Octanol on the Permeability Coefficient of Mannitol

| % of Saturation | Permeability Coefficient ± SEM |
|---|---|
| 0 | $8.49 \times 10^{-6} \pm 2.32 \times 10^{-6}$ |
| 26.7 | $2.32 \times 10^{-5} \pm 8.02 \times 10^{-6}$ |
| 55.6 | $1.48 \times 10^{-5} \pm 6.71 \times 10^{-6}$ |
| 84.4 | $4.22 \times 10^{-5} \pm 1.55 \times 10^{-5}$ |
| 100 | $5.35 \times 10^{-3} \pm 4.18 \times 10^{-3}$ |
| 222.2 | $8.74 \times 10^{-3} \pm 5.05 \times 10^{-3}$ |

As can be seen in TABLE 8, at 8 hours the saturating levels of octanol (100% and 222.2%) provided increases in the permeability coefficient of approximately 126 fold or more over octanol at 84.4% of saturation. In contrast, the octanol at 84.4% of saturation provided an increase of only about five fold in comparison to the control without any octanol.

We claim:

1. A composition useful for the enhancement of the transdermal delivery of a medicament, comprising an effective amount of the medicament suspended in
   (a) a formulation comprising an aqueous solution of lower alcohol, where the concentration of the lower alcohol is between about 10% and about 35% by volume of the solution, and
   (b) higher alcohol selected from the group consisting of 1-hexanol, 1-octanol, 1-nonanol, 1-decanol, 1-undecanol, 1-dodecanol, 1-tridecanol, 1-tetradecanol, 4-methyl-1-pentanol, 5-methyl-1-heptanol, 3,3-dimethyl-1-octanol, 3-cyclopentyl-1-propanol, cis-3-hexen-1-ol, trans-3-hexen-1-ol, 9-decen-1ol and 2-octanol, said higher alcohol being present in an amount that is sufficient to substantially saturate the composition.

2. A composition according to claim 1 wherein the concentration of the lower alcohol is between about 20% to about 30% by volume of the solution.

3. A composition according to claim 1 wherein the medicament is selected from the group consisting of calcium channel blocking agents, beta-blocking agents, sympathomimetic drugs, analgesics, antihistamines, and antipsychotics.

4. A composition according to claim 1 wherein the composition is prepared in the form of a gel.

5. A composition according to claim 4 wherein the gel is prepared as a hydrogel of cross-linked polyvinylpyrrolidone.

6. A method of preparing a composition useful for the enhancement of the transdermal delivery of a medicament, comprising the steps of
   (a) suspending an effective amount of the medicament in a formulation comprising an aqueous solution of lower alcohol, where the concentration of the lower alcohol is between about 10% and about 35% by volume of the solution, and
   (b) adding higher alcohol selected from the group consisting of 1-hexanol, 1-octanol, 1-nonanol, 1-decanol, 1-undecanol, 1-dodecanol, 1-tridecanol, 1-tetradecanol, 4-methyl-1-pentanol, 5-methyl-1-heptanol, 3,3-dimethyl-1-octanol, 3-cyclopentyl-1-propanol, cis-3-hexen-1-ol, trans-3-hexen-1-ol, 9-decen-1-ol and 2-octanol, said higher alcohol being present in an amount that is sufficient to substantially saturate the composition.

* * * * *

UNITED STATES PATENT AND TRADEMARK OFFICE
CERTIFICATE OF CORRECTION

PATENT NO. : 5,149,719
DATED : September 22, 1992
INVENTOR(S) : Richard H. Ferber; Scott A. Burton It is certified that error appears in the above-indentified patent and that said Letters Patent is hereby corrected as shown below:

Col. 5, line 24, "7th" should read --17th--

Col. 8, line 18, "H:-Mannitol" should read --$H^3$-Mannitol--

Col. 12, line 33, "Hi9her" should read --Higher--

Col. 16, line 29, "9-decen-1ol" should read --9-decen-1-ol--

Signed and Sealed this

First Day of March, 1994

*Attest:*

BRUCE LEHMAN

*Attesting Officer*  *Commissioner of Patents and Trademarks*